United States Patent [19]

Frachet et al.

[11] Patent Number: 5,144,952
[45] Date of Patent: Sep. 8, 1992

[54] TRANSCUTANEOUS CONNECTION DEVICE

[75] Inventors: Bruno Frachet, Montmorency; Michel Y. David, Paris, both of France

[73] Assignee: Assistance Publique, Paris, France

[21] Appl. No.: 533,789

[22] Filed: Jun. 6, 1990

[30] Foreign Application Priority Data

Jun. 7, 1989 [FR] France .................. 89 07557
Apr. 2, 1990 [FR] France .................. 90 04191

[51] Int. Cl.⁵ .............................................. A61B 5/04
[52] U.S. Cl. .................................. 128/642; 128/420.6
[58] Field of Search .................. 381/68.3, 68.6; 128/420.5, 420.6, 642; 600/25

[56] References Cited

U.S. PATENT DOCUMENTS

| 4,495,917 | 1/1985 | Byers | 128/420.6 |
| 4,510,936 | 4/1985 | Fourcin | 128/420.6 |
| 4,612,915 | 9/1986 | Hough | 600/25 |
| 4,617,913 | 10/1986 | Eddington | 128/420.6 |
| 4,923,469 | 5/1990 | Fiachet | 128/420.5 |
| 4,932,405 | 6/1990 | Peeters | 128/420.6 |

FOREIGN PATENT DOCUMENTS

0241307 10/1987 European Pat. Off. ......... 128/420.6

Primary Examiner—Kyle L. Howell
Assistant Examiner—Robert L. Nasser, Jr.
Attorney, Agent, or Firm—Wenderoth, Lind & Ponack

[57] ABSTRACT

A transcutaneous connection device connects an electrical stimulator outside the body to at least one subcutaneous electrical conductor. Cutaneous penetration is afforded by a system placed in the pinna of the ear or in the earlobe and connected on the one hand to the electrical stimulator and on the other hand to the subcutaneous electrical conductor.

29 Claims, 6 Drawing Sheets

TRANSCUTANEOUS CONNECTION DEVICE

BACKGROUND OF THE INVENTION

The present invention relates to a transcutaneous connection device serving to connect a bioelectrical stimulation apparatus outside the body to one or more subcutaneous electrical conductors, and more particularly to an electrode designed for electrical stimulation of the inner ear in the case of complete sensorineural deafness or tinnitus.

The use of electrical stimulations is extensive, whether muscle or nerve stimulation. The electrical excitation can be delivered indirectly or directly:

indirectly, through the skin, which remains intact, using a device with two induction coils subjected to a high-frequency current (conventional implantation technique)

directly, via a metallic conductor which passes through the skin. This method of direct excitation simplifies the generating system, but risks cutaneous complications, essentially of an infectious type.

SUMMARY OF THE INVENTION

The present invention is based on the idea of using the pinna of the ear for producing a device for direct transcutaneous connection.

The present invention therefore relates to a transcutaneous connection device designed to connect an electrical stimulator outside the body to at least one subcutaneous electrical conductor, characterized in that the cutaneous penetration is afforded by means of a system placed in the pinna of the ear and connected on the one hand to the electrical stimulator and on the other hand to the subcutaneous electrical conductor.

In a first embodiment of the invention, the system placed in the pinna of the ear is positioned in a fold of the pinna situated below the navicular furrow and advantageously comprises at least one subcutaneous conducting wire covered with an insulating sheath, fixed to a ball of conducting metal positioned on the surface of the pinna of the ear and covered with an insulating material on the part of its outer surface in contact with the pinna of the ear, the conducting wire and the ball preferably being made of platinum-iridium, the insulating material and sheath advantageously being made of a biocompatible insulating material, preferably Teflon (i.e. a trademark for polytetrofluoroethylene) and Parylene ® (i.e. a trademark for a family of thermopolastic polymers including poly-p-xylene and variations thereof).

In a second embodiment, the system placed in the pinna of the ear consists of an earring positioned in the earlobe.

The earring advantageously comprises on the one hand a rod connected to a subcutaneous assembly comprising at least one conducting wire of which the distal end is connected to the subcutaneous electrical conductor and the proximal end to the rod, and on the other hand a clasp connected to the electrical stimulator outside the body.

The rod of the earring is advantageously insulated by means of a biocompatible plastic sheath.

In the two embodiments of the invention, the conducting wire is preferably coiled, for example in such a way as to form a spring, and is made of a biocompatible material; which is advantageously Phynox ® (i.e. a trademark for an austenitic alloy having about the composition 40% Co, 20% Cr, 16% Ni and 7% Mo), the coiled conducting wire being covered by a biocompatible insulating material, preferably Parylene ® (i.e. a trademark for a family of thermopolastic polymers including poly-p-xylene and variations thereof).

According to another preferred alternative embodiment of the invention, the transcutaneous connection device comprises three subcutaneous conducting wires coiled in such a way as to form three interlaced helical springs, or comprises three conducting wires braided together.

The conducting wire affording the connection between the subcutaneous electrical conductor and the rod of the earring or the ball placed under the navicular furrow can be connected to the subcutaneous electrical conductor by any appropriate means.

A first appropriate means consists in the subcutaneous electrical conductor and the conducting wire connected to the conducting ball or the earring being joined to one another by welding.

A second appropriate means consists of a splice formed, for example, in the mastoid process by surgical intervention.

A third appropriate means consists of at least two electrical connectors, each connector advantageously consisting of a composite piece which comprises a male part forming a pin and a female part forming a socket in which the male part forming the pin of the other connector engages.

The conducting ball or the earring are connected to the external stimulator by any appropriate means. However, preference is given to means which can be removed under the action of a force of predetermined value. In the case of the conducting ball, these means preferably consist of a metallic or metallized ear-piece matching the contours of the pinna of the ear.

The ball is positioned advantageously by snapping it into a cavity formed in the ear-piece, of shape and dimensions corresponding essentially to those of the ball, the cavity being insulated from the ear-piece and its surface being connected to the external stimulator and constituting the active pole, the metallic mass or the metallized surface of the ear-piece forming an ground contact with the skin of the pinna and of the auditory canal.

In the case of the earring, the removable link between the stimulation apparatus and the earring is advantageously formed by means of a magnet, preferably of cylindrical shape, fixed on the earring on which there is applied a magnetic mass consisting preferably of a second magnet of the same shape connected to the outlet of the stimulator.

The first magnet is advantageously fixed in one of the branches of the clasp of the earring by means of a metallic conductive sheath fixed in the branch of the clasp by welding, in such a way that an edge of the metallic conducting sheath projects relative to the magnet in such a way as to receive the second magnet connected to the outlet of the external stimulator, the two magnets being oriented for a reciprocal attraction upon connection.

BRIEF DESCRIPTION OF THE DRAWINGS

Other characteristics and advantages of the invention will emerge from the following detailed description, with reference to the attached drawings, in which.

FIG. is a perspective view of a portion of a device similar to that shown in FIG. 12, but illustrating three conducting wires in the form of interlaced helical springs.

DETAILED DESCRIPTION OF THE INVENTION

Figure 1:
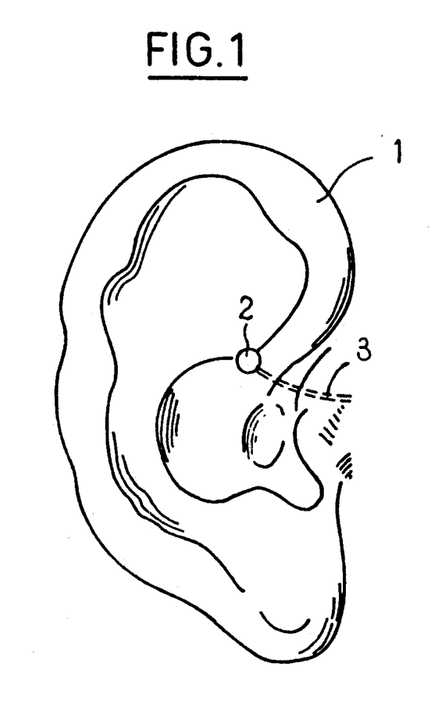
FIG. 1 is a view of the pinna of an ear, indicating the position of a transcutaneous connection device according to a first embodiment of the invention.

In the first embodiment of the invention, the device is fixed on the pinna of an ear 1 in a fold in the latter situated below the navicular furrow, as illustrated in FIG. 1, and mounting means in the form of a ball 2 situated on the surface of the pinna of the ear and connected to a subcutaneous conducting wire 3, advantageously by welding.

The ball 2 advantageously has a diameter of approximately 3 mm and, like the conducting wire 3, is made of a platinum-iridium alloy.

The conducting wire 3 and the surface of the ball 2 in contact with the skin of the pinna of- the ear are insulated by means of a covering or sheath 7 which is advantageously made of Teflon (i.e. a trademark for polytrafluoroethylene) and Parylene ® (i.e. a trademark fro a family of thermoplastic polymers including poly-p-xylene and variations thereof). The conducting wire 3 perforates the cutaneous surface and is directed towards a connection with a subcutaneous electrical conductor consisting, for example, of a stimulation electrode placed in the inner ear.

Figure 2:
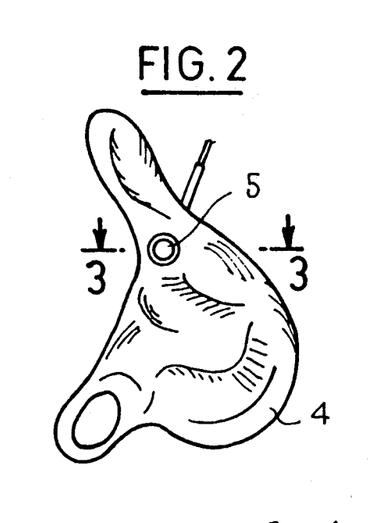
FIG. 2 is a view of an ear-piece affording an electrical link between the transcutaneous connection device according to the first embodiment of the invention and an external stimulator.

The ball 2 is connected to an external stimulator (not shown) by means of a metallic or metallized earpiece 4 matching the contours of the pinna of the ear, as represented in FIG. 2.

The ear-piece 4 is advantageously made of gold and is fashioned from an impression formed by molding and reproducing with the greatest possible precision the contours of the pinna of the ear, in particular those of the concha and of the subnavicular furrow.

The ear-piece 4 includes a member 5 defining a cavity of shape and dimensions corresponding to those of the ball 2.

Figure 3:
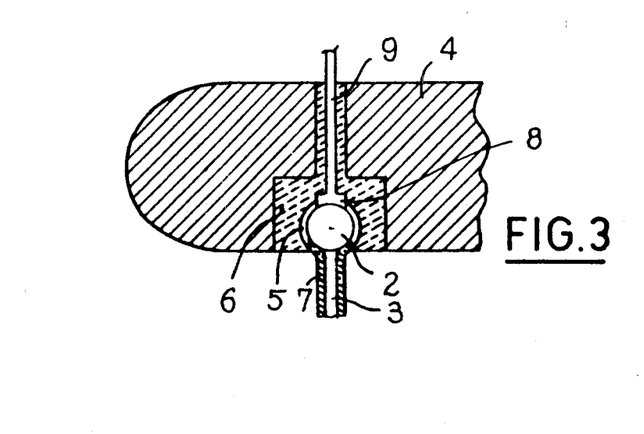
FIG. 3 is a longitudinal cutaway view of the ear-piece represented in FIG. 2, connected to a ball according to the first embodiment of the invention.

The ear-piece 4 connected to the external stimulator is placed in contact with the pinna of the ear, its anterior face visible in FIG. 2 coming to bear in contact with the skin of the pinna in such a way that the ball 2 is in line with the cavity of members 5 and snaps into the latter as represented in FIG. 3.

The member 5 defining the cavity is insulated from the ear-piece 4 by means of an insulating sheath 6. The ball 2 is fixed to the conducting wire 3 surrounded by an insulating sheath 7, the latter covering the outer surface of the ball 2 in order to insulate ball 2 from the skin of the pinna of the ear. When it is positioned in the cavity by snapping therein, the ball 2 comes to bear in contact with a flattened end 8 of a wire 9 connected to the external stimulator, the member 5 thus forming an active pole, the metallic ear-piece 4 affording a ground contact with the skin of the pinna of the ear and of the auditory canal.

Figure 4:
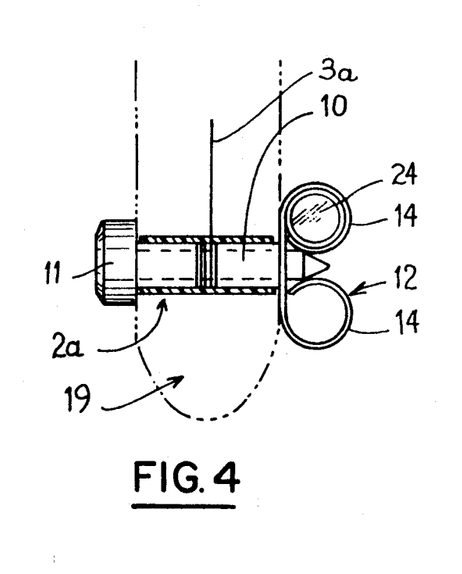
FIG. 4 is a longitudinal cutaway view of an earlobe, fitted with a device according to a second embodiment of the invention.
Figure 5:
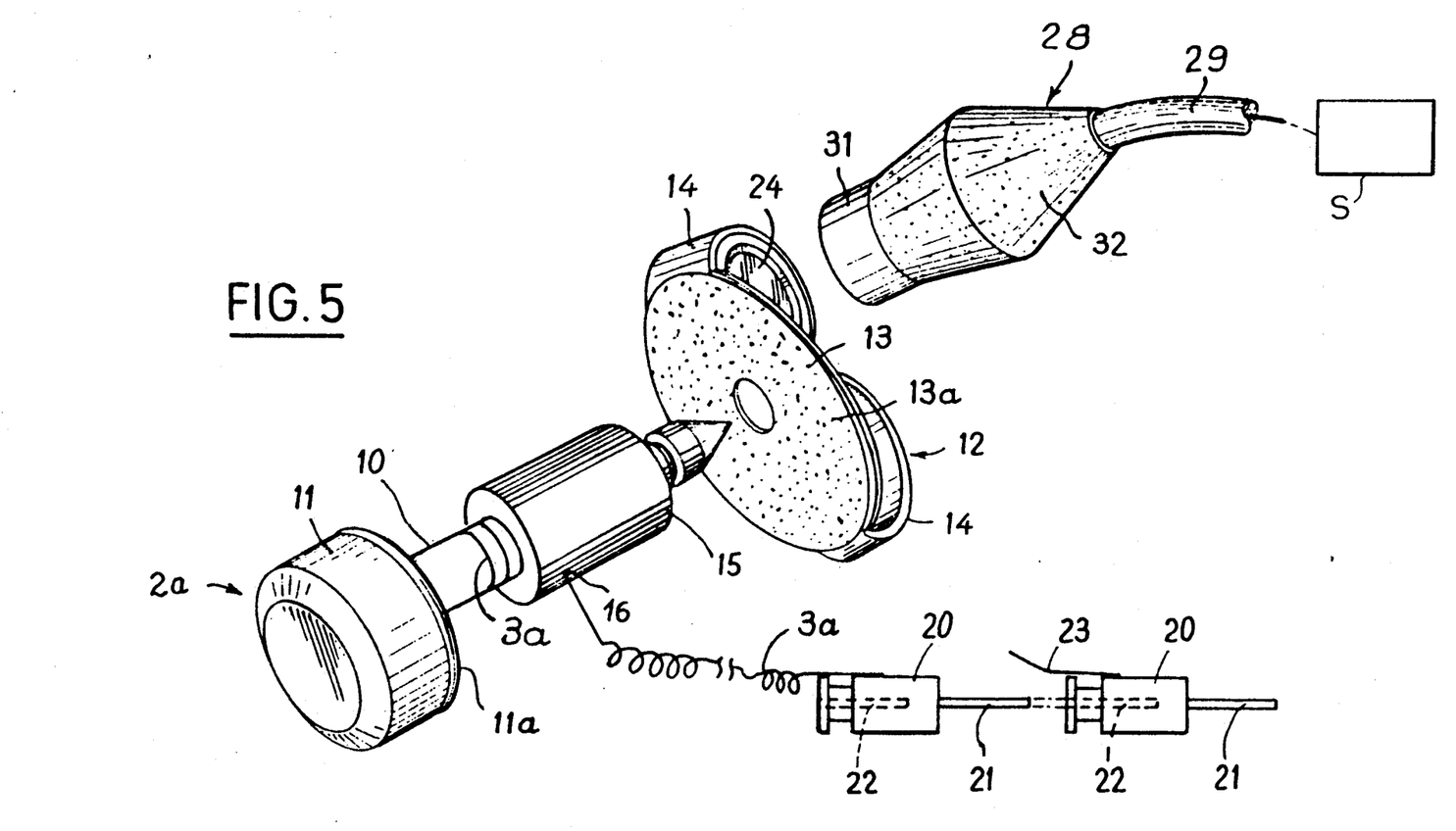
FIG. 5 is an exploded perspective view, partially cut away, of the device according to the second embodiment of the invention, with its means for connection to the external stimulator, in which view the device is disconnected from the external stimulator.

In the second embodiment of the invention, the device is fixed to the earlobe 19, as illustrated in FIGS. 4 and 5. It comprises an earring 2a fixed in the earlobe 19. The earring 2a comprises a rod 10 passing through the earlobe and has at its front end a unit 11 and at its rear end a clasp 12 which comprises a central disk 13, perforated to allow the rod 10 to pass therethrough, and two branches 14 curved over themselves in each case to form a tube.

The central disk 13 and the inner face of the unit 11 are advantageously insulated from the earlobe by means of an insulating disk 13a and by an insulating plate 11a respectively.

The rod 10 of the earring is connected to a wire 3a coiled to form a spring, made of an electrically conductive material such as Phynox ® (i.e. a trademark for an austenitic alloy having about the composition 40% Co, 20% Cr, 16% Ni and 7% Mo), placed in the earlobe by surgical intervention, the coiled wire itself being connected to a subcutaneous electrical conductor.

The wire 3a is insulated along its subcutaneous course by means of a sheath formed, from a biocompatible insulating material such as the above mentioned Parylene ®.

The distal end of the wire 3a is connected to the subcutaneous electrical conductor, which can consist of a wire, connected to a stimulation electrode, such as that described in French patent FR-2,613,575 (corresponding to U.S. Pat. No. 4,923,469), used in the case of complete deafness or in the treatment of tinnitus.

Figure 12:
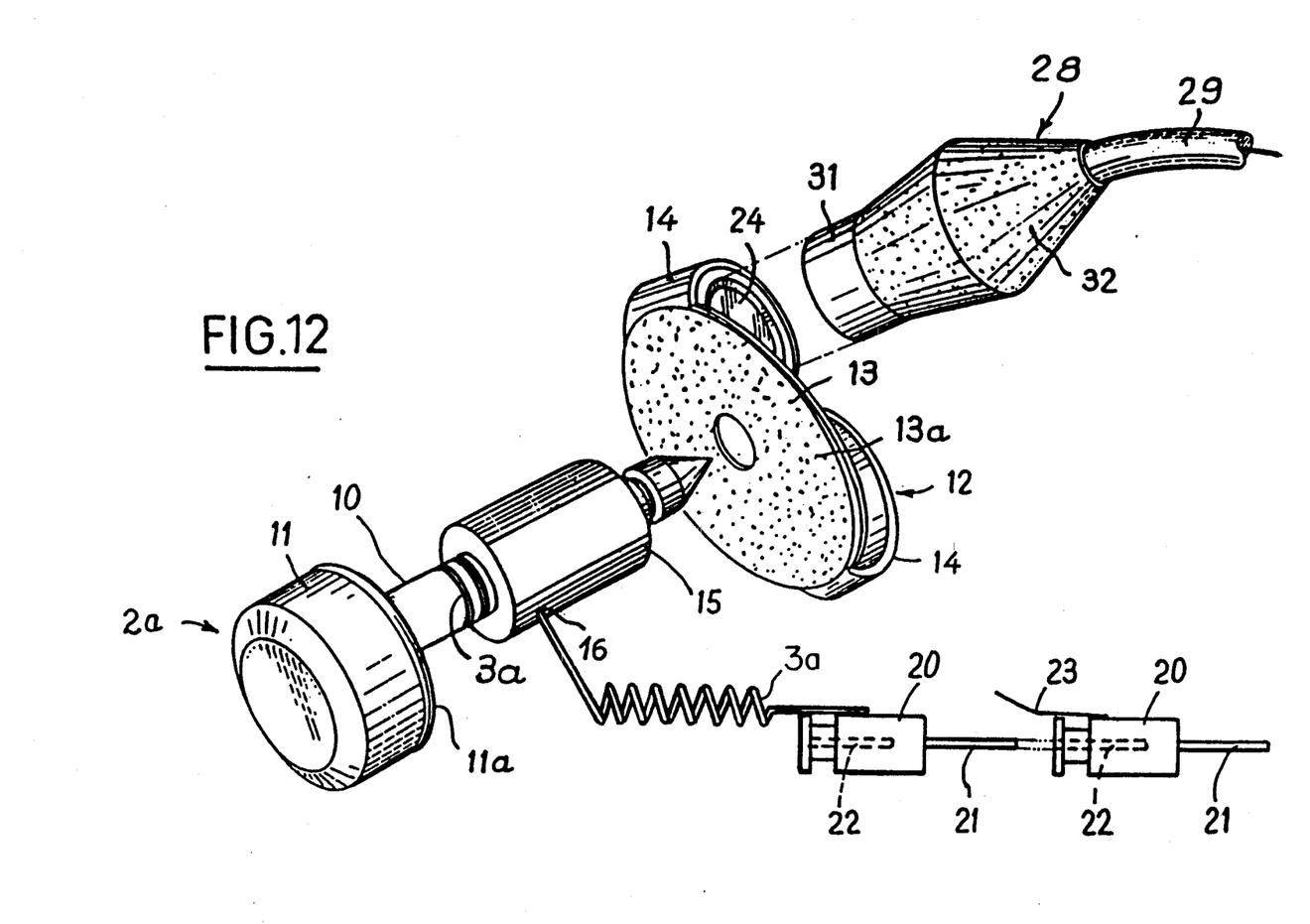
FIG. 12 is a view similar to FIG. 5, but showing a conducting wire having the shape of a helical spring.
Figure 13:
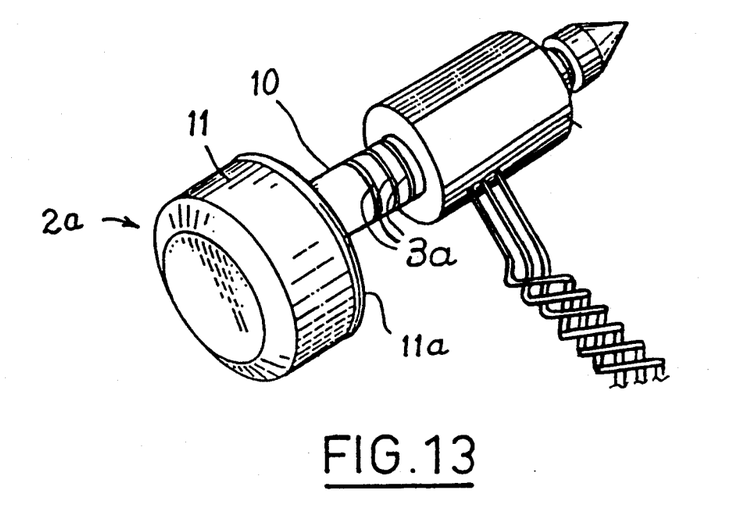
Figure 14:
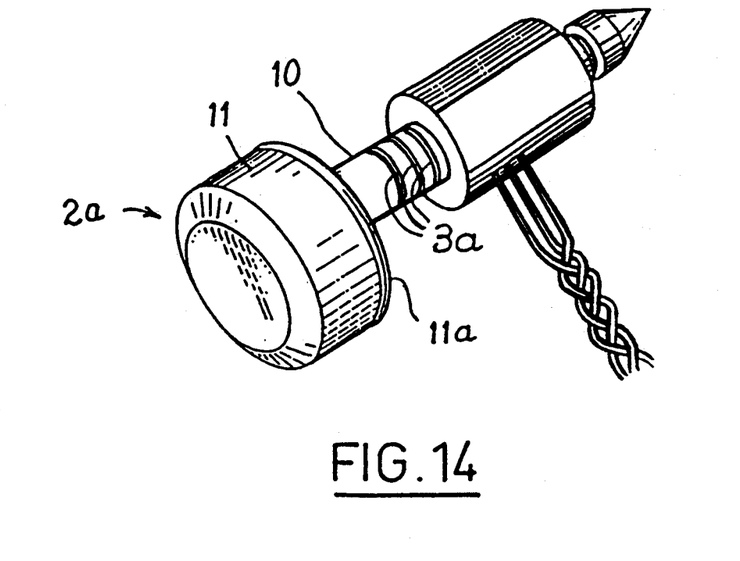
FIG. 14 is a view similar to FIG. 13, but wherein the three conducting wires are braided together.

The conducting wire 3a can be twisted as shown in FIG. 5 or coiled to form a spring, e.g. a helical spring, as shown in FIG. 12. Further, the transcutaneous connection device may include plural subcutaneous conducting wires, e.g. three such wires coiled to form three interlaced helical springs as shown in FIG. 13 or braided together as shown in FIG. 14.

The subcutaneous electrical conductor can also consist of any single or multiple electrical conductor designed for the stimulation of a nerve or muscle structure.

In the case where the device according to the invention is designed to connect to an electrode applied on the oval window of the inner ear, the positioning of the stimulation electrode and of the transcutaneous connection device is carried out during the same surgical intervention. The wire 3a is connected to the subcutaneous conductor, for example to a wire ending at the stimulation electrode, by means of a weld, a splice formed in the mastoid process during the surgical intervention, or else by means of small electrical connectors.

The proximal end of the wire 3a is wound around the rod 10 of the earring. The rod 10 of the earring 2a and the wire 3a wound round the latter are insulated by means of an insulating plastic sheath 15 which preferably consists of a catheter portion, the wire 3a perforating this insulating sheath at position 16 situated advantageously at the middle of the rod 10.

The wire 3a can also be bent and simply slipped under the insulating sheath 15.

FIG. 5 represents in addition two electrical connectors 20 designed to afford another type of connection between the wire 3a and the subcutaneous electrical conductor, other than a weld or a splice.

Each connector 20 consists of a composite piece comprising a male part forming a pin 21 and female part forming a socket 22.

A first of the connectors 20 is connected to the conducting wire 3a by means of, for example, a weld. The male part forming the pin 21 of this first connector can then engage in the female part forming the socket 22 of a second connector 20 connected to the subcutaneous electrical conductor 23, which is connected, for example, to the stimulation electrode of the inner ear described hereinabove.

The connection is established by the surgeon at the time of positioning of the transcutaneous connection system according to the invention. It can be made up of a number of connectors greater than two, stacked one in the other by means of their male and female parts, and connected to as many subcutaneous conductors.

This system of connection by means of small stacked connectors can of course be used in all the embodiments of the subcutaneous device of the invention, including the device consisting of the ball 2 and the wire 3.

Figure 6:
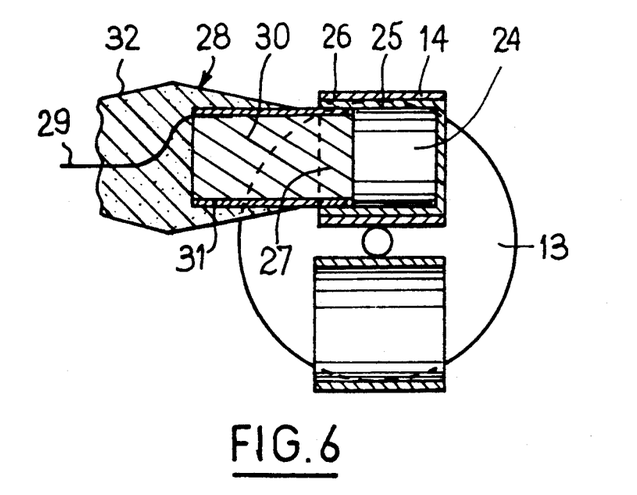
FIG. 6 is a cutaway view of connection means connecting the device in FIG. 5 to the external stimulator.

FIG. 6 represents a cutaway view of the system for connecting the device of the second embodiment according to the invention to the bioelectrical stimulator.

A small magnet 24 i fixed in one of the branches 14 of the clasp 12 by means of a conductive metallic sheath 25 welded in the branch of the clasp, the magnet advantageously being of cylindrical shape and the assembly being of a diameter substantially equal to that formed by the fold of the branch 14. The length of the magnet 24 is advantageously shorter than the length of the sheath 25 in such a way that an axial end or edge 26 of the electroconductive metallic sheath projects beyond the magnet 24 and forms a space in the shape of a nose or recess 27 into which may be fit a second magnet 30. The two magnets 24 and 30 are oriented by a reciprocal attraction in such a way as to afford an optimum electrical contact.

A connector 28 is provided at the end of a wire, 29 leaving the stimulation apparatus 5 and includes a small magnetic mass, which advantageously is the small magnet 30 likewise having the shape of a cylinder whose diameter is slightly smaller than that of the magnet 24. This magnet 30 is covered on its outer peripheral surface by a sheath 31 of electroconductive metal.

The sheath 31 is designed to connect the conducting wire 29 to the magnet 30 and it additionally affords electrical conduction between the bioelectrical stimulator and the branch 14 of the clasp of the earring 2a, which is also afforded by means of the magnet 30 which is sufficiently electrically conductive. The connection of the wire 29 leaving the stimulation apparatus with the magnet 30 is protected by means of a sheath 32 made of polymeric resin. Electric current is then transmitted via the bias of the rod 10 to the wire 3a.

The wire 3a thus transmits electrical impulses to the subcutaneous electrical conductor, for example by way of a weld, a splice (not shown) made in the mastoid process, or by way of the small electrical connectors shown in FIG. 5, to a wire connected to an electrical stimulation electrode applied on the membrane of the oval window.

In the description of the second embodiment of the invention, a single pole is taken into consideration. The other, i.e. ground, consists of a reference electrode which is, for example, in the case of a device connecting a stimulation electrode placed in the inner ear, a wide molded electrode placed in the concha of the ear, of the ear-piece type described hereinabove, which thus constitutes a cutaneous mass of good surface area. Any other ground electrode is, however, conceivable. In particular, the earring can have several connections, one of which is a ground connection.

The subcutaneous electrical conductor can consist of a wire connected to a stimulation electrode such as that described in French patent FR 2,613,575, used in the case of complete deafness or in the treatment of tinnitus.

The subcutaneous electrical conductor can also consist of any single or multiple electrical conductor designed for the stimulation of a nerve or muscle structure.

In the case where the device according to the invention is designed to connect an electrode applied on the oval window of the inner ear, the positioning of the stimulation electrode and of the transcutaneous connection device is carried out during the same surgical intervention.

As indicated hereinabove, several subcutaneous conducting wires can be provided. In such case it is also necessary to provide an equal number of external conductors forming the link with the external stimulator. For example, it is possible to provide a three-conductor link, and FIGS. 7 to 11 illustrate connection means between three subcutaneous wires and three external conductors.

Figure 7:
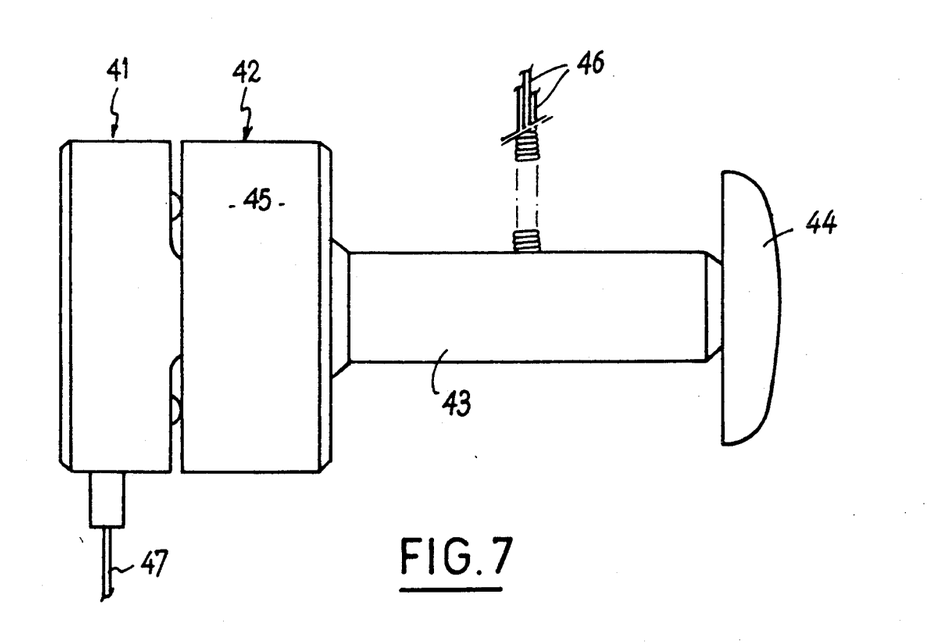
FIG. 7 is an elevation view of an alternative embodiment of the means for connection to the external stimulator.

These connection means consist of a male connector 41 and a female connector 42. The female connector comprises a rod 43 which passes through the pinna of the ear and which has, at one of its ends, a button 44 which comes to bear on the pinna of the ear and, at its other end, the actual housing 45 of the female connector.

Three subcutaneous conductors 46, which are wound one upon the other in such a way as to form three interlaced helical springs, are shown in FIG. 7. Three external conductors 47 emerge laterally from the male element 41.

Figure 8:
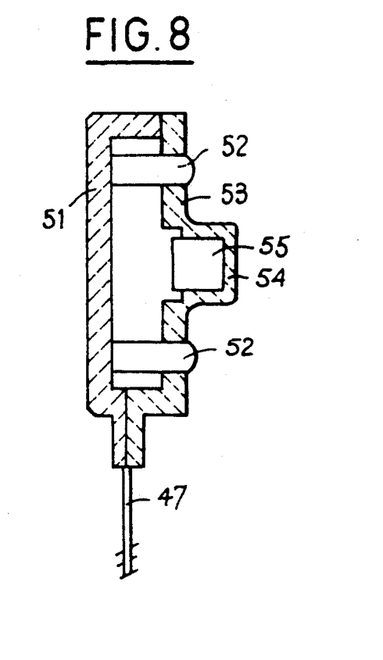
FIG. 8 is an axial cutaway view of the male connector of the connection means in FIG. 7.
Figure 9:
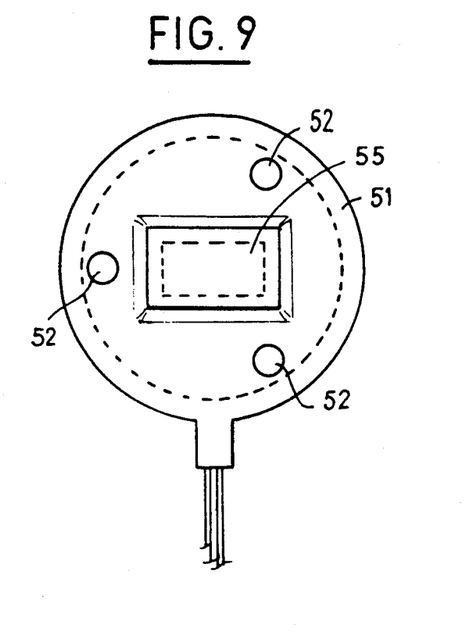
FIG. 9 is a view from the right of FIG. 8.

FIGS. 8 and 9 represent the male connector in detail. It consists of a circular casing 51 in which three conducting pins 52 are arranged with uniform angular spacing. These three pins project from one face 53 of the casing 51. This face also has projecting therefrom a central rectangular part 54 which also constitutes a seat for a magnet 55. The free ends of the pins 52 are of rounded shape.

Figure 10:
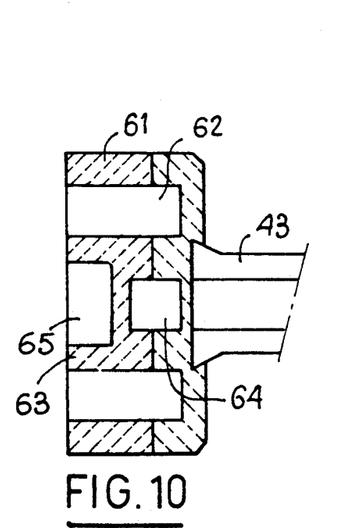
FIG. 10 is an axial cutaway view of the end of a female connector of the connection means in FIG. 7.
Figure 11:
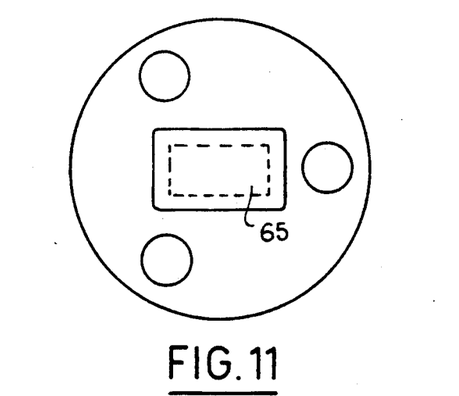
FIG. 11 is a view from the left of FIG. 10.

FIGS. 10 and 11 represent the functional part of the female connector housing 45; that includes a casing 61 in which are housed pins 62 which are arranged in an arrangement analogous to that of the pins 52 of the male connector. One end of each of the pins 62 is positioned inwardly of one of the faces 63 of the casing 61, the free outer surface of each of the pins 62 being situated flush with face 63. The casing 61 includes an inner axial seat in which a magnet 64 is housed.

Extending inwardly from face 63 is a recess 65 of rectangular shape corresponding to that of the projecting part 54 of the male connector. These two elements 54 and 65 constitute a polarizing slot affording correct connection of the pins 52 on the pins 62. As in the other embodiments, the contact pressure therebetween is affored by the magnetic forces created by the two magnets 55 and 64.

All the conducting elements are advantageously made of the same material and are connected to one another by autogenous welding or splicing in such a way as to avoid the undesirable effects of electrochemical couples created by the junction of two different materials.

The transcutaneous connection device to which the invention relates is very reliable and easy to handle, especially in view of the fact that it is connected to the bioelectrical stimulation apparatus outside the body by means of a removable connection and that a simple movement of the hand suffices to disconnect it.

It is used in the field of complete deafness or tinnitus, but also in the treatment of non-auditory problems such as the stimulation of nerve or muscle structures, for example the stimulation of stumps or the electrical treatment of localized pains.

We claim:

1. A transcutaneous connection device for connecting an electrical stimulator to be located exterior of a body of a suer of the device to at least one electrical conductor to be located subcutaneously of the body, said device comprising:
   at least one subcutaneous conducting wire adapted to be connected to the electrical conductor, said conducting wire being covered with an insulating sheath;
   mounting means having a construction to be mounted on the pinna of an ear of the body;
   means for electrically attaching said mounting means to said conducting wire; and
   connection means having a construction to be mounted exteriorly of the pinna of the ear for electrically connecting said mounting means to the electric stimulator.

2. A device as claimed in claim 1, wherein said mounting means comprises a ball-shaped member to be mounted on the surface of the pinna of the ear, and said attaching means comprises a weld joining said ball-shaped member to an end of said conducting wire.

3. A device as claimed in claim 2, wherein a surface of said ball-shaped member to contact skin of the pinna of the ear is covered with an insulating sheath.

4. A device as claimed in claim 2, wherein said conducting wire and said ball-shaped member are formed of platinum-iridium.

5. A device as claimed in claim 2, wherein said connection means comprises a metal or metallized ear piece having a shape matching the contours of the pinna of the ear and having a cavity matching the shape of said ball-shaped member, such that when the ear piece is mounted on the pinna of the ear said ball-shaped member snaps into said cavity.

6. A device as claimed in claim 1, wherein said mounting means comprises an earring including a rod to extend through the pinna of the ear, and a clasp fitting on said rod to maintain said rod in position on the pinna.

7. A device as claimed in claim 6, wherein said rod is insulated by a biocompatible sheath.

8. A device as claimed in claim 6, wherein said attaching means comprises an electrical connection of said conducting wire to said rod.

9. A device as claimed in claim 6, wherein said connection means comprises means for attaching the electrical stimulator to said earring by means enabling detachment under the action of a force of predetermined value.

10. A device as claimed in claim 9, wherein said connection means comprises a magnet.

11. A device as claimed in claim 10, wherein said magnet is fixed to said earring.

12. A device as claimed in claim 11, wherein said connection means further comprises a magnetic mass to be fixed to an output of the electrical stimulator.

13. A device as claimed in claim 12, wherein said magnetic mass comprises another magnetic of the same shape as said first mentioned magnet.

14. A device as claimed in claim 13, wherein said first mentioned magnet is fixed in a conductive metallic sheath fixed in a branch of said clasp with an edge of said metallic sheath projecting beyond said first mentioned magnet and defining a recess, and said another magnet fits in said recess with said magnets aligned in mutual reciprocal attraction.

15. A device as claimed in claim 14, wherein said metallic sheath is welded to said clasp.

16. A device as claimed in claim 13, wherein said magnets are cylindrically shaped.

17. A device as claimed in claim 6, comprising a plurality of conducting wires connected to said rod.

18. A device as claimed in claim 17, wherein said connection means comprises an assembly for connecting said conducting wires to the electrical stimulator.

19. A device as claimed in claim 18, wherein said assembly comprises a male member and a female member joinable to each other by a respective projection and an irregularly shaped recess.

20. A device as claimed in claim 19, further comprising magnet means for maintaining said members in joined position.

21. A device as claimed in claim 18, wherein said female member has therein plural conducting pins electrically connected to respective of said plurality of conducting wires, and said male member has a plurality of conducting pins to be connected to respective of a plurality of external conductors of the electrical stimulator, said pins of said male member contacting respective pins of said female member in a joined position of said members.

22. A device as claimed in claim 1, wherein said conducting wire is twisted.

23. A device as claimed in claim 1, wherein said conducting wire is in the shape of a helical spring.

24. A device as claimed in claim 1, wherein said conducting wire is formed of an austenitic alloy including about 40% Co, 20% Cr, 16% Ni and 7% Mo.

25. A device as claimed in claim 1, wherein said insulating sheath is formed of a polymer of paraxylene.

26. A device as claimed in claim 1, comprising three said conducting wires coiled to form three interlaced helical springs.

27. A device as claimed in claim 1, comprising three said conducting wires braided together.

28. A device as claimed in claim 1, further comprising a connector structure for connecting said conducting wire to the electrical conductor.

29. A device as claimed in claim 28, wherein said connector structure comprises at least two electrical connectors each having a male part in the form of a pin and a female part in the form of a socket, with the pin of one said connector being received in the socket of another said connector.

* * * * *